United States Patent [19]

Merrill

[11] Patent Number: 6,121,323
[45] Date of Patent: Sep. 19, 2000

[54] BISHYDROXYUREAS

[75] Inventor: Bryon A. Merrill, River Falls, Wis.

[73] Assignee: 3M Innovative Properties Company, St. Paul, Minn.

[21] Appl. No.: 08/984,477

[22] Filed: Dec. 3, 1997

[51] Int. Cl.[7] .......................... C07C 279/18; A61K 31/17
[52] U.S. Cl. .......................... 514/597; 514/826; 514/863; 564/49; 564/50; 564/51
[58] Field of Search .................................. 564/50, 51, 49; 514/597, 826, 863

[56] References Cited

U.S. PATENT DOCUMENTS

| | | | |
|---|---|---|---|
| 3,174,991 | 3/1965 | Steinbrunn | 260/465 |
| 3,623,984 | 11/1971 | Carlos | 252/47.5 |
| 4,330,606 | 5/1982 | Sobel et al. | 130/17 |
| 4,728,670 | 3/1988 | Haslanger et al. | 514/484 |
| 5,468,760 | 11/1995 | Malamas et al. | 514/374 |
| 5,504,097 | 4/1996 | Malamas et al. | 514/365 |
| 5,516,789 | 5/1996 | Brooks et al. | 514/414 |
| 5,541,205 | 7/1996 | Malamas et al. | 514/364 |
| 5,612,377 | 3/1997 | Crooks et al. | 514/596 |
| 5,792,882 | 8/1998 | Kawai et al. | 562/623 |

FOREIGN PATENT DOCUMENTS

| | | |
|---|---|---|
| 1127344 | 4/1962 | Germany . |
| 1129151 | 5/1962 | Germany . |
| 1133360 | 7/1962 | Germany . |
| 1135890 | 9/1962 | Germany . |
| 2415603 | 10/1974 | Germany . |
| 96/32377 | 10/1996 | WIPO . |

OTHER PUBLICATIONS

J. E. Everard et al., "Nitroxide Biradicals from Substituted Bis(Hydroxy–Ureas)", *Organic Magnetic Resonance*, 12, No. 6, 383–384 (1979).

K. A. Ohemeng et al., "Novel Bishydroxamic Acids as 5–Lipoxygenase Inhibitors", *Bioorganic & Medicinal Chemistry*, 2, No. 3, 187–193 (1994).

*Primary Examiner*—Peter O'Sullivan
*Attorney, Agent, or Firm*—MarySusan Howard; Ted K. Ringsred; Robert W. Sprague

[57] ABSTRACT

Bishydroxyureas are provided that inhibit the enzyme 5-lipoxygenase. These compounds have the formula I

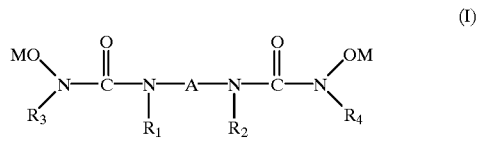

(I)

wherein $R_1$, $R_2$, $R_3$, $R_4$, A and M are defined herein. Also disclosed are pharmaceutical compositions containing such compounds and methods of inhibiting the enzyme 5-lipoxygenase using such compounds.

6 Claims, No Drawings

BISHYDROXYUREAS

FIELD OF THE INVENTION

This invention relates to bishydroxyurea compounds that are useful to inhibit the 5-lipoxygenase mediated metabolism of arachidonic acid. In another aspect this invention relates to pharmaceutical compositions comprising bishydroxyureas. A further aspect of this invention relates to methods of treating diseases mediated by products of the 5-lipoxygenase pathway in a subject in need thereof by administering a bishydroxyurea compound to the subject.

BACKGROUND OF THE INVENTION

An important biosynthetic pathway for the metabolism of arachidonic acid is initiated by the enzyme 5-lipoxygenase (5-LO). The first product formed by the oxidation of arachidonic acid with 5-LO is 5-hydroperoxyeicosatetraenoic acid (5-HPETE) which is subsequently converted to either 5-hydroxyeicosatetraenoic acid (5-HETE) or the leukotriene intermediate $LTA_4$. Further enzymatic metabolism of $LTA_4$ leads to the production of $LTB_4$ and the peptidoleukotrienes ($LTC_4$, $LTD_4$, and LTE4).

The above mentioned biosynthetic products of the 5-LO pathway are very potent substances. When present in the nanomolar to picomolar concentration range, these compounds produce a variety of biological effects which are associated with mammalian disease. For example, 5-HETE stimulates tumor growth in epithelial and squamous cell based cancers. The peptidoleukotrienes are known to be potent constrictors of human airway smooth muscle; aerosol administration of these substances to non-asthmatic volunteers has been shown to induce bronchoconstriction. Both $LTB_4$ and 5-HETE are potent chemotactic factors for inflammatory cells such as polymorphonuclear leukocytes, and both compounds have been isolated in the synovial fluids of arthritic patients.

Disease states in which leukotrienes are important mediators include: adult respiratory distress syndrome, allergic rhinitis, arthritis, asthma, chronic obstructive pulmonary disease, gout, inflammatory bowel disease, ischemic induced myocardial injury, psoriasis, reperfusion injury, spinal cord injury, stroke, and traumatic brain injury.

A chemical compound which acts as an inhibitor of the 5-LO enzyme should be an effective therapeutic agent for the treatment or prevention of these diseases, as well as any other disease which is mediated by products of the 5-LO pathway.

SUMMARY OF THE INVENTION

Certain bishydroxyurea compounds have been found that inhibit 5-lipoxygenase (5-LO). These compounds are useful in the treatment of disease states that are mediated by products of the 5-LO pathway, including leukotrienes and 5-HETE. Accordingly, the invention provides compounds of Formula I:

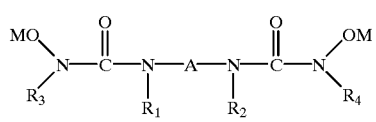

wherein $R_1$, $R_2$, $R_3$, $R_4$, A and M are defined below.

The invention also provides a pharmaceutical composition comprising a therapeutically effective amount of a compound of Formula I and a pharmaceutically acceptable vehicle. Further, this invention provides a method of inhibiting the enzyme 5-lipoxygenase in an animal and a method of treating an animal having a condition responsive to such inhibition, comprising administering to the animal a compound of Formula I in an amount effective to inhibit 5-lipoxygenase.

DETAILED DESCRIPTION OF THE INVENTION

The bishydroxyurea compounds of this invention are compounds of Formula I

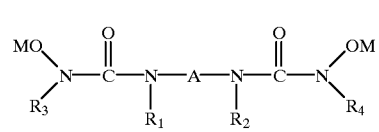

wherein $R_1$, $R_2$, $R_3$, $R_4$, A and M have the following meanings:

$R_1$ and $R_2$ are independently selected from the group consisting of hydrogen and $C_{1-6}$ straight or branched chain alkyl. Preferably $R_1$ and $R_2$ are the same. More preferably, $R_1$ and $R_2$ are hydrogen.

$R_3$ and $R_4$ are independently selected from the group consisting of $C_{1-14}$ straight or branched chain alkyl optionally substituted by a group selected from halogen, nitro, hydroxyl, carboxyl and amino, and optionally interrupted by —O—, —S(O)$_{0-2}$—, —NR— wherein R is as defined below, or —CO—; and arylalkyl wherein the alkyl group is straight or branched chain and has from one to eight carbon atoms and the aryl group is phenyl optionally substituted with one or more substituents selected from the group consisting of $C_{1-6}$ straight or branched chain alkyl and halogen. Preferably $R_3$ and $R_4$ are the same and are selected from the group consisting of $C_{1-6}$ straight or branched chain alkyl and phenylalkyl wherein the alkyl group is straight or branched chain and has from one to eight carbon atoms. More preferably $R_3$ and $R_4$ are the same and are selected from the group consisting of methyl, isopropyl, 1-ethylpropyl and benzyl.

A is selected from the group consisting of:
  (a) phenylene optionally substituted with one or more substituents selected from the group consisting of $C_{1-6}$ straight or branched chain alkyl and halogen;
  (b) $C_{3-8}$ cycloalkylene;
  (c) $C_{1-12}$ straight or branched chain alkylene;
  (d) naphthalene optionally substituted with one or more substituents selected from the group consisting of $C_{1-6}$ straight or branched chain alkyl and halogen;
  (e)

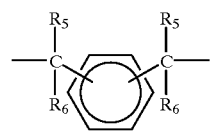

wherein each $R_5$ and $R_6$ is independently selected from the group consisting of hydrogen and $C_{1-3}$ straight or branched chain alkyl; and (f)

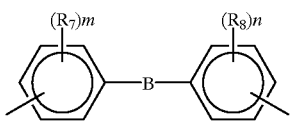

wherein each $R_7$ and $R_8$ is independently selected from the group consisting of hydrogen, $C_{1-3}$ straight or branched chain alkyl, $C_{1-3}$ alkoxy, and halogen;

m is 1 or 2;

n is 1 or 2; and

B is selected from the group consisting of
(i) a carbon-carbon bond;
(ii) oxy;
(iii) thio;
(iv) sulfone;
(v) carbonyl;

(vi)

wherein R is selected from the group consisting of hydrogen and $C_{1-3}$ straight or branched chain alkyl;

(vii) —$(CH_2)_p$— wherein p is an integer from 1 to 14; and (viii)

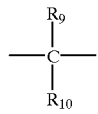

wherein $R_9$ and $R_{10}$ are independently selected from the group consisting of hydrogen, $C_{1-3}$ straight or branched chain alkyl, $C_{3-6}$ cycloalkyl, and trifluoromethyl.

Preferably A is selected from the group consisting of (a) $C_{1-12}$ straight or branched chain alkylene and (b)

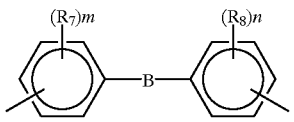

When A is

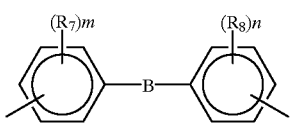

the urea groups are preferably bonded at the para position of each ring. Preferably $R_7$ and $R_8$ are the same and are selected from the group consisting of hydrogen, $C_{1-3}$ straight or branched chain alkoxy and chloro and m and n are both 1. More preferably $R_7$ and $R_8$ are hydrogen or chloro.

Preferably B is selected from the group consisting of:
(a) a carbon-carbon bond;
(b) oxy; and (c)

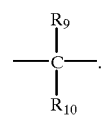

When B is

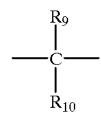

preferably $R_9$ and $R_{10}$ are the same and are selected from the group consisting of hydrogen and trifluoromethyl. More preferably B is methylene or oxy.

M is selected from the group consisting of hydrogen, a pharmaceutically acceptable cation, and a pharmaceutically acceptable metabolically cleavable group. Preferably, M is hydrogen.

The term "pharmaceutically acceptable cation" refers to nontoxic cations well known to those skilled in the art and including but not limited to those based on the alkali and alkaline earth metals such as sodium, lithium, potassium, magnesium, aluminum and the like, as well as nontoxic ammonium, quaternary ammonium, and amine cations derived from nitrogenous bases of sufficient basicity to form salts with the N-hydroxy group of compounds of Formula I where M is hydrogen.

The term "metabolically cleavable group" denotes a moiety that is readily cleaved in vivo from the compound bearing it. The compound remains or becomes pharmacologically active after cleavage. Metabolically cleavable groups are generally derived from compounds known to those skilled in the art that are reactive with the N-hydroxy group of compounds of Formula I where M is hydrogen. Such groups include, but are not limited to, alkanoyl such as acetyl, propionyl, and the like, unsubstituted and substituted aroyl such as benzoyl and substituted benzoyl, alkoxycarbonyl such as ethoxycarbonyl and the like, monoesters formed from dicarboxylic acids such as succinyl, unsubstituted and substituted carbamoyl such as dimethylcarbamoyl and so on. Compounds bearing metabolically cleavable groups can act as prodrugs and may exhibit improved bioavailability over the parent compound.

The invention is inclusive of compounds that can exist in multiple isomeric forms. These individual forms, including enantiomers and diastereomers as well as mixtures of the various forms, are part of the invention.

Preferred compounds include compounds of Formula II:

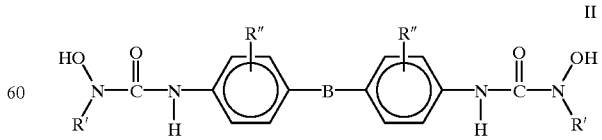

wherein R', R" and B are as defined below.

R' is selected from the group consisting of $C_{1-14}$ straight or branched chain alkyl and benzyl. Preferred R' groups include methyl, isopropyl, 1-ethylpropyl and benzyl.

R" is selected from the group consisting of hydrogen, $C_{1-3}$ straight or branched chain alkyl, halogen, and $C_{1-3}$ straight or branched chain alkoxy. Preferably R" is hydrogen or chloro.

B is selected from the group consisting of:
(a) a carbon-carbon bond;
(b) oxy; and (c) 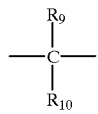

wherein $R_9$ and $R_{10}$ are the same and are selected from the group consisting of hydrogen and trifluoromethyl.

B is preferably oxy or methylene.

Preferred compounds of the invention include:
4,4'-Methylenebis(1-hydroxy-1-isopropyl-3-phenylurea);
4,4'-Methylenebis(1-hydroxy-1-benzyl-3-phenylurea);
4,4'-Methylenebis(1-hydroxy-1-methyl-3-(2,6-diethylphenyl)urea);
4,4'-Oxybis(1-hydroxy-1-methyl-3-phenylurea);
1,1'-(m-Phenylene)bis(3-hydroxy-3-methylurea);
1,1'-(1,5-Naphthalene)bis(3-hydroxy-3-methylurea);
trans-1,4-Cyclohexanebis(3-hydroxy-3-methylurea);
1,1'-Hexamethylenebis(3-hydroxy-3-benzylurea);
1,1'-(4,4'-(2,2'-Dimethoxy)biphenyl)bis(3-hydroxy-3-methylurea);
1,1'-(m-Phenylene)bis(1-methyl-1-(3-hydroxy-3-(1-ethylpropyl)ureido)ethane);
1,1'-(p-Phenylene)bis(3-hydroxy-3-(1-ethylpropyl)urea);
1,1'-(4-Methyl-m-phenylene)bis(3-hydroxy-3-(1-ethylpropyl)urea);
1,1'-(2-Methylpentamethylene)bis(3-hydroxy-3-(1-ethylpropyl)urea); and
1,1'-Octamethylenebis(3-hydroxy-3-(1-ethylpropyl)urea).

Particularly preferred compounds of the invention include:
4,4'-Methylenebis(1-hydroxy-1-methyl-3-phenylurea);
4,4'-(2,2-Hexafluoropropane)bis(1-hydroxy-1-methyl-3-phenylurea);
4,4'-Methylenebis(1-hydroxy-1-(1-ethylpropyl)-3-phenylurea); and
4,4'-Oxybis(1-hydroxy-1-(1-ethylpropyl)-3-phenylurea); and
4,4'-Methylenebis(1-hydroxy-1-(1-ethylpropyl)-3-(2-chlorophenyl)urea).

Compounds of the invention can be prepared in accordance with the Reaction Schemes described below or through modifications thereof that will be readily apparent to those skilled in the art. A suitable route can be selected with due consideration of the particular $R_1$, $R_2$, $R_3$, $R_4$, A and M substituents, availability of starting materials and the like.

Compounds of the invention where $R_1$, $R_2$ and M are all hydrogen and $R_3$ and A are as defined above can be prepared according to Reaction Scheme I.

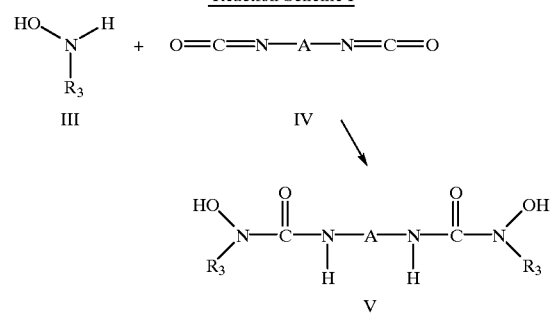

Reaction Scheme I

Reaction Scheme I involves reacting a hydroxylamine of Formula III with a diisocyanate of Formula IV to provide a bishydroxyurea of Formula V. Many hydroxylamines of Formula III are commercially available. Others may be readily prepared using conventional methods, for example, by conversion of a suitable aldehyde or ketone to its oxime followed by reduction to the hydroxylamine. Many diisocyanates of Formula IV are also commercially available. Others may readily be prepared using conventional methods, for example, Curtius rearrangement, Hofmann rearrangement, Schmidt reaction, or by reacting a suitable diamine with phosgene or a phosgene equivalent (e.g. 1,1'-carbonyldiimidazole or 1,1'-carbonylbisbenzotriazole). The reaction in Reaction Scheme I can be conducted at ambient temperature by combining the hydroxylamine and the diisocyanate in a suitable solvent (e.g. an organic solvent such as diethyl ether, tetrahydrofuran, dichloromethane). When a salt (e.g. hydrochloride) of the hydroxylamine is used, it is converted to the free base using conventional means (e.g. reacting with one equivalent of base in a suitable solvent) prior to its reaction with the diisocyanate.

The compounds of Formula I wherein M is a pharmaceutically acceptable cation can be prepared by combining a compound of Formula I wherein M is hydrogen with a relatively strong base, e.g., a base of the formula $M(OH)_x$ wherein M is the pharmaceutically acceptable cation and x is the valence of such cation in a polar solvent. Isolation of the salt can be facilitated by the addition of a solvent in which the salt is insoluble.

Compounds of Formula I in which $R_3$ and $R_4$ are different can be prepared by reacting one mole of a diisocyanate of Formula IV sequentially with one mole of a hydroxylamine of formula $R_3NHOH$ and one mole of a hydroxylamine of formula $R_4NHOH$ and isolating the desired bishydroxyurea from the resulting mixture using conventional separation techniques (e.g., flash chromatography, selective recrystallization).

Compounds of Formula I in which $R_1$ and $R_2$ are other than hydrogen and $R_3$ and $R_4$ are the same can be prepared by the reaction of one mole of a diamine with two moles of phosgene or a phosgene equivalent (e.g. 1,1'-carbonyldiimidazole or 1,1'-carbonylbisbenzotriazole) followed by two moles of a hydroxylamine of the formula $R_3NHOH$.

Compounds of Formula I in which $R_1$, $R_2$, $R_3$, $R_4$, $R_1$ and $R_8$ are as defined above and A is

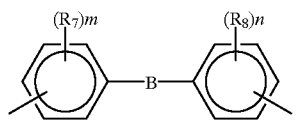

can be prepared by palladium catalyzed coupling of appropriately functionalized hydroxyurea precursors when B is a carbon-carbon bond or methylene (such as the Stille or Suzuki coupling reactions); and can be prepared by copper catalyzed coupling of appropriately functionalized hydroxyurea precursors when B is oxy (such as the Ullmann Reaction).

A compound of Formula I can be formulated for various routes of administration (e.g. oral, topical, parenteral) in an appropriate pharmaceutically acceptable vehicle suitable for the selected dosage form. Suitable excipients and preparation of pharmaceutical compositions are well known to those skilled in the art and disclosed, e.g. in *Remington's Pharmaceutical Sciences*, 18th Edition, 1990, Mack Publishing Company.

A pharmaceutical composition of the invention comprises a therapeutically effective amount of a compound of Formula I. The amount that constitutes a therapeutically effective amount will depend on the particular compound, the particular formulation, the route of administration, and the intended therapeutic effect. Those skilled in the art can readily determine a therapeutically effective amount with due consideration of such factors.

Compounds of Formula I have been shown to inhibit the enzyme 5-lipoxygenase, and therefore have utility in treating conditions mediated by products of the 5-lipoxygenase pathway. Such conditions include but are not limited to adult respiratory distress syndrome, allergic rhinitis, arthritis, asthma, cancer, chronic obstructive pulmonary disease, gout, inflammatory bowel disease, ischemic induced myocardial injury, psoriasis, reperfusion injury, spinal cord injury, stroke, and traumatic brain injury.

The examples below are given to further illustrate the invention. The particular materials used and amounts thereof, as well as other conditions and details, should not be construed to limit the invention.

EXAMPLE 1

4,4'-Methylenebis(1-hydroxy-1-methyl-3-phenylurea)

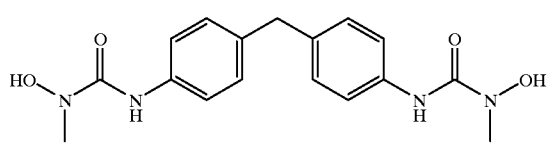

A mixture of N-methylhydroxylamine-hydrochloride (2.5 g, 30 mmol), water (5 ml), and diethyl ether (100 ml) was cooled to 0° C. and NaOH (1.3 g dissolved in 10 ml of water) was added dropwise over a 10 min period. The mixture was maintained at 0° C. for 10 min followed by the addition of 4,4'-methylenebis(phenylisocyanate) (2.5 g, 10 mmol) as a solid. A white precipitate formed immediately. After 0.5 h, the cooling bath was removed and the reaction was maintained at ambient temperature for 15 h. The reaction was filtered to provide a white powder. Recrystallization from N,N-dimethylformamide\water yielded 2.0 g of the desired product as white plates: MP: 196.0° C. (decomp); $^1$H NMR (300 MHz, DMSO): δ 9.70 (s, 2H), 8.86 (s, 2H), 7.48 (d, J=8.5 Hz, 4H), 7.06 (d, J=8.5 Hz, 4H), 3.78 (s, 2H), 3.04 (s, 6H); $^{13}$C NMR (75 MHz, DMSO): δ 157.9, 137.2, 135.2, 128.3, 119.3, 39.9, 38.1; MS (FAB): m/e 345.1560 (345.1563 calc'd for $C_{17}H_{21}N_4O_4$, M+H); Anal. calc'd for $C_{17}H_{20}N_4O_4$: C, 59.29; H, 5.85; N, 16.27. Found: C, 59.30; H, 5.82; N, 16.36.

EXAMPLE 2

4,4'-Methylenebis(1-hydroxy-1-isopropyl-3-phenylurea)

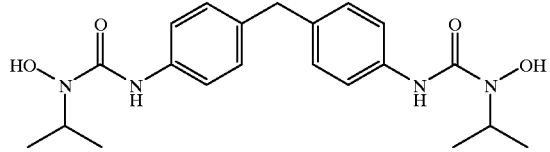

The same general procedure as reported in Example 1 was followed. 4,4'-Methylenebis(phenylisocyanate) (2.0 g, 8 mmol), N-isopropylhydroxylamine-hydrochloride (2.7 g, 24 mmol), NaOH (1.1 g dissolved in 10 ml of water), diethyl ether (100 ml), and water (5 ml) were combined. Filtration of the reaction mixture yielded 2.9 g of the desired product as a white powder. Recrystallization from N,N-dimethylformamide\water provided an analytically pure sample: MP: 219.0° C. (decomp); $^1$H NMR (300 MHz, DMSO): δ 9.24 (s, 2H), 8.82 (s, 2H), 7.50 (d, J=8.5 Hz, 4H), 7.06 (d, J=8.5 Hz, 4H), 4.30 (septet, J=6.6 Hz, 2H), 3.78 (s, 2H) 1.06 (d, J=6.6 Hz, 12H); $^{13}$C NMR (75 MHz, DMSO): δ 156.9, 136.7, 134.7, 127.8, 118.7, 47.9, 39.4, 18.1; MS (FAB): m/e 401.2189 (401.2189 calc'd for $C_{21}H_{29}N_4O_4$, M+H); Anal. calc'd for $C_{21}H_{28}N_4O_4$: C, 62.98; H, 7.05; N, 13.99. Found: C, 63.04; H, 6.96; N, 13.85.

EXAMPLE 3

4,4'-Methylenebis(1-hydroxy-1-benzyl-3-phenylurea)

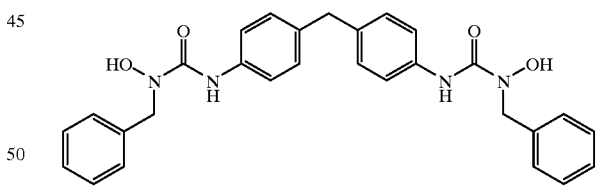

The same general procedure as reported in Example 1 was followed. 4,4'-Methylenebis(phenylisocyanate) (2.0 g, 8 mmol), N-benzylhydroxylamine-hydrochloride (3.9 g, 24 mmol), NaOH (1.1 g dissolved in 10 ml of water), diethyl ether (100 ml), and water (5 ml) were combined. Filtration of the reaction mixture yielded 3.7 g of the desired product as a pale tan powder. Recrystallization from N,N-dimethylformamide\water provided an analytically pure sample: MP: 189.0° C. (decomp); $^1$H NMR (300 MHz, DMSO): δ 9.90 (s, 2H), 8.92 (s, 2H), 7.52 (d, J=8.6 Hz, 4H), 7.33–7.21 (m, 10 H), 7.08 (d, J=8.6 Hz, 4H), 4.63 (s, 4H), 3.79 (s, 2H); $^{13}$C NMR (75 MHz, DMSO): δ 157.2, 137.6, 137.2, 135.2, 128.3, 128.0, 126.8, 119.3, 53.2, 39.9; IR (KBr): 3379, 3062, 2919, 2852, 1621, 1595, 1549, 1419, 1226, 1089, 775, 696 cm$^{-1}$; MS (FAB): m/e 497.2206 (497.2188 calc'd for $C_{29}H_{29}N_4O_4$, M+H); Anal. calc'd for $C_{29}H_{28}N_4O_4$: C, 70.15; H, 5.68; N, 11.28. Found: C, 70.23; H, 5.63; N, 11.28.

EXAMPLE 4

4,4'-Methylenebis(1-hydroxy-1-methyl-3-(2,6-diethylphenyl)urea)

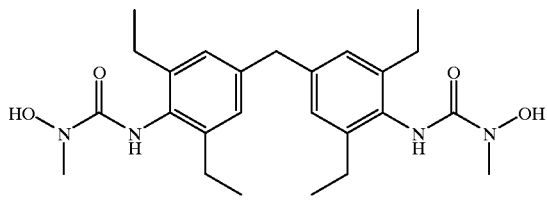

The same general procedure as reported in Example 1 was followed. 4,4'-Methylenebis(2,6-diethylphenylisocyanate) (3.6 g, 10 mmol), N-methylhydroxylamine-hydrochloride (2.5 g, 30 mmol), NaOH (1.3 g dissolved in 15 ml of water), diethyl ether (100 ml), and water (5 ml) were combined. The product formed as a precipitate. Recrystallization from N,N-dimethylformamide\water provided 1.8 g of the desired product as a white powder: MP: 257.0° C. (decomp); $^1$H NMR (300 MHz, DMSO): δ 9.61 (s, 2H), 8.16 (s, 2H), 6.93 (s, 4H), 3.83 (s, 2H), 3.00 (s, 6H), 2.50–2.43 (q, J=7.5 Hz, 8H) 1.09–1.04 (t, J=7.5 Hz, 12H); IR (Nujol): 3409, 1623, 1603, 1526, 1395, 1342, 1182, 1119 cm$^{-1}$; MS (FAB): m/e 457.2828 (457.2815 calc'd for $C_{25}H_{37}N_4O_4$, M+H); Anal. calc'd for $C_{25}H_{36}N_4O_4$: C, 65.76; H, 7.95; N, 12.27. Found: C, 65.62; H, 7.99; N, 12.31.

EXAMPLE 5

4,4'-(2,2-Hexafluoropropane)bis(1-hydroxy-1-methyl-3-phenylurea)

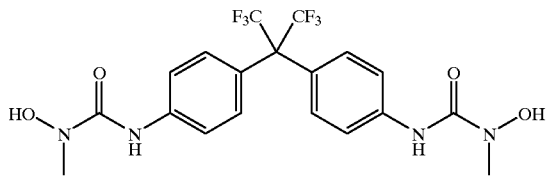

The same general procedure as reported in Example 1 was followed. 2,2-Bis(4-isocyanatophenyl)hexafluoropropane (2.0 g (5.2 mmol) dissolved in 25 ml of diethyl ether), N-methylhydroxylamine-hydrochloride (1.3 g, 15.5 mmol), NaOH (0.7 g dissolved in 10 ml of water), diethyl ether (50 ml), and water (5 ml) were combined. The product formed as a precipitate. Recrystallization from N,N-dimethylformamide\water provided 0.72 g of the desired product as a fine white powder: MP: 182.0° C. (decomp); $^1$H NMR (300 MHz, DMSO): δ 9.90 (broad s, 2H), 9.30 (broad s, 2H), 7.70 (d, J=8.8 Hz, 4H), 7.19 (d, J=8.8 Hz, 4H), 3.08 (s, 6H); $^{13}$C NMR (75 MHz, DMSO): δ 157.2, 140.1, 129.4, 125.1, 124.6 (q, J=284 Hz), 118.5, 37.6; IR (KBr): 3332, 3047, 2822, 1598, 1550, 1422, 1364, 1248, 1177, 968, 957, 930, 835, 827 cm$^{-1}$; MS (FAB): m/e 481.1317 (481.1310 calc'd for $C_{19}H_{19}N_4O_4F_6$, M+H); Anal. calc'd for $C_{19}H_{18}N_4O_4F_6$: C, 47.51; H, 3.78; N, 11.66. Found: C, 47.45; H, 3.68; N, 11.88.

EXAMPLE 6

4,4'-Oxybis(1-hydroxy-1-methyl-3-phenylurea)

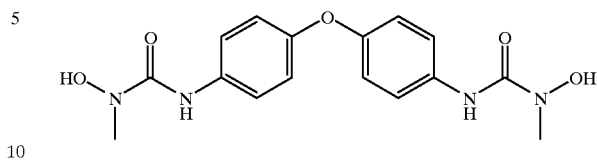

The same general procedure as reported in Example 1 was followed. 4,4'-oxybis(phenylisocyanate) (2.36 g, 10 mmol), N-methylhydroxylamine-hydrochloride (2.5 g, 30 mmol), NaOH (1.3 g dissolved in 10 ml of water), diethyl ether (100 ml), and water (5 ml) were combined. The product formed as a precipitate. Recrystallization from N,N-dimethylformamide\water provided 1.8 g of the desired product as a white powder: MP: 183.0–184.0° C.; $^1$H NMR (300 MHz, DMSO): δ 9.71 (s, 2H), 8.96 (s, 2H), 7.59–7.56 (d, J=9.0 Hz, 4H), 6.89–6.86 (d, J=9.0 Hz, 4H), 3.06 (s, 6H); $^{13}$C NMR (75 MHz, DMSO): δ 157.8, 151.7, 134.6, 120.7, 118.0, 38.0; IR (KBr): 3365, 3145, 2895, 1639, 1554, 1505, 1412, 1344, 1304, 1262, 1221, 1196, 1012, 876, 847, 814 cm$^{-1}$; Anal. calc'd for $C_{16}H_{18}N_4O_4$: C, 55.49; H, 5.24; N, 16.18. Found: C, 55.54; H, 5.30; N, 16.11.

EXAMPLE 7

1,1'-(m-Phenylene)bis(3-hydroxy-3-methylurea)

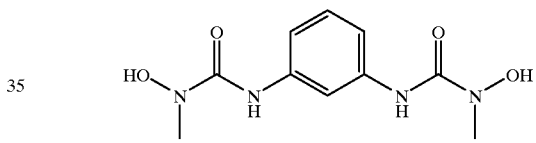

The same general procedure as reported in Example 1 was followed. 1,3-Phenylene diisocyanate (2.0 g, 12.5 mmol), N-methylhydroxylamine-hydrochloride (3.1 g, 37 mmol), NaOH (1.6 g dissolved in 10 ml of water), diethyl ether (120 ml), and water (5 ml) were combined. Filtration of the reaction mixture provided 3.1 g of the desired product as a light tan powder: MP: 146.0–147.0° C.; $^1$H NMR (300 MHz, DMSO): δ 9.80 (broad s, 2H), 8.77 (s,2H), 7.80 (t, J=1.9 Hz, 1H), 7.20–7.06 (m, 3H), 3.05 (s, 6H); $^{13}$C NMR (75 MHz, DMSO): δ 157.8, 139.2, 128.0, 113.6, 110.8, 38.1; IR (KBr): 3400, 3182, 2898, 1660, 1616, 1544, 1498, 1344, 802, 737, 696, 607 cm$^{-1}$; MS (FAB): m/e 255.1076 (255.1093 calc'd for $C_{10}H_{15}N_4O_4$, M+H).

EXAMPLE 8

1,1'-(1,5-Naphthalene)bis(3-hydroxy-3-methylurea)

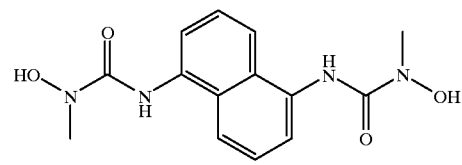

The same general procedure as reported in Example 1 was followed. 1,5-Naphthalene diisocyanate (2.1 ml, 10 mmol), N-methylhydroxylamine-hydrochloride (2.5 g, 30 mmol), NaOH (1.3 g dissolved in 10 ml of water), diethyl ether (100 ml), and water (5 ml) were combined. The product formed as a precipitate. Recrystallization from N,N-dimethylformamide\water provided 1.4 g of the desired product as a white crystalline solid: MP: 190.0–191.0° C. (decomp); $^1$H NMR (300 MHz, DMSO): δ 9.92 (s, 2H), 9.00 (s, 2H), 7.73 (d, J=8.4 Hz, 2H), 7.61 (d, J=7.0 Hz, 2H), 7.51–7.46 (m, 2H), 3.12 (s, 6H); $^{13}$C NMR (75 MHz, DMSO): δ 158.4, 134.0, 128.4, 125.0, 120.5, 118.4, 38.1; IR (KBr): 3413, 3170, 2874, 1646, 1537, 1506, 1451, 1402, 1347, 1261, 1173, 1122, 897, 778, 754, 715 cm$^{-1}$; MS (FAB): m/e 305.1250 (305.1250 calc'd for $C_{14}H_{17}N_4O_4$, M+H); Anal. calc'd for $C_{14}H_{16}N_4O_4$: C, 55.26; H, 5.30; N, 18.41. Found: C, 55.04; H, 5.26; N, 18.37.

EXAMPLE 9 trans-1,4-Cyclohexanebis(3-hydroxy-3-methylurea)

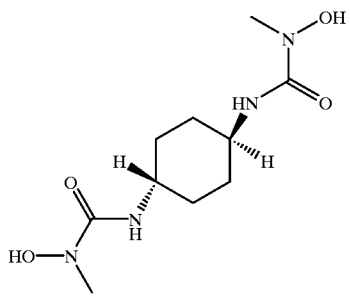

The same general procedure as reported in Example 1 was followed. 1,4-Cyclohexane diisocyanate (2.5 g, 15 mmol), N-methylhydroxylamine-hydrochloride (3.8 g, 45 mmol), NaOH (2.0 g dissolved in 10 ml of water), diethyl ether (120 ml), and water (5 ml) were combined. Filtration of the reaction mixture provided 3.8 g of the desired product as an off-white powder: MP: 186° C. (decomp); $^1$H NMR (300 MHz, DMSO): δ 9.36 (broad s, 2H), 6.56–6.53 (d, J=8.5 Hz, 2H), 3.35 (broad s, 2H), 2.92 (s, 6H), 1.76–1.64 (m, 4H), 1.36–1.29 (m, 4H); $^{13}$C NMR (75 MHz, DMSO): δ 160.2, 47.9, 38.7, 31.7; MS (FAB): m/e 261.1557 (261.1563 calc'd for $C_{10}H_{21}N_4O_4$, M+H).

EXAMPLE 10

1,1'-Hexamethylenebis(3-hydroxy-3-benzylurea)

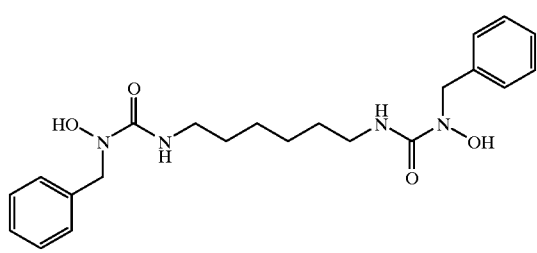

The same general procedure as reported in Example 1 was followed. 1,6-Diisocyanatohexane (1.3 ml, 8.1 mmol), N-benzylhydroxylamine-hydrochloride (3.2 g, 20 mmol), NaOH (1.0 g dissolved in 10 ml of water), diethyl ether (100 ml), and water (5 ml) were combined. Filtration of the reaction mixture yielded 3.2 g of the desired product as a white powder. Recrystallization from N,N-dimethylformamide\water provided an analytically pure sample: MP: 181.0–182.0° C.; $^1$H NMR (300 MHz, DMSO): δ 9.26 (s, 2H), 7.34–7.20 (m, 10H), 6.94–6.89 (t, J=5.9 Hz, 2H), 4.50 (s, 4H), 3.08–3.01 (q, J=6.6 Hz, 4H), 1.43–1.20 (m, 8H); $^{13}$C NMR (75 MHz, DMSO): δ 160.4, 138.0, 128.0, 127.8, 126.6, 54.0, 39.4, 29.9, 26.1; IR (KBr): 3381, 3140, 2887, 1595, 1540, 1246, 1223, 1116, 744, 723, 694 cm$^{-1}$; MS (FAB): m/e 415.2361 (415.2345 calc'd for $C_{22}H_{31}N_4O_4$, M+H); Anal. calc'd for $C_{22}H_{30}N_4O_4$: C, 63.75; H, 7.30; N, 13.52. Found: C, 63.55; H, 7.49; N, 13.59.

EXAMPLE 11

1,1'-(4,4'-(2,2'-Dimethoxy)biphenyl)bis(3-hydroxy-3-methylurea)

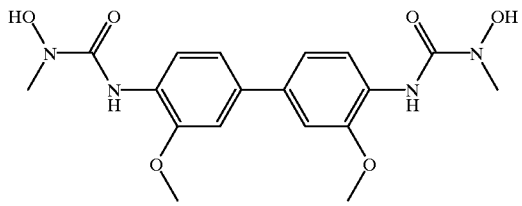

A solution of N-methylhydroxylamine-hydrochloride (1.1 g, 13.2 mmol), water (5 ml), and tetrahydrofuran (60 ml) was cooled to 0° C. and NaOH (0.65 g in 7 ml water) was added dropwise over a 10 min period. The reaction was maintained at 0° C. for 10 min followed by the addition of dianisidine diisocyanate (1.5 g, 5.1 mmol). A precipitate formed within 5 min. The cooling bath was removed and the reaction was maintained at ambient temperature overnight. Filtration yielded 1.9 g of the desired product as a tan powder. Recrystallization from N,N-dimethylformamide\water provided an analytically pure sample: MP: 205° C. (decomp); $^1$H NMR (300 MHz, DMSO): δ 10.10 (s, 2H), 8.43 (s, 2H), 8.14 (d, J=8.4 Hz, 2H), 7.29 (d, J=1.9 Hz, 2H), 7.25–7.22 (dd, J=8.4, 1.9 Hz, 2H), 3.96 (s, 6H), 3.10 (s, 6H); $^{13}$C NMR (75 MHz, DMSO): δ 157.1, 147.6, 134.2, 126.7, 118.5, 117.5, 108.7, 56.0, 37.9; IR (KBr): 3399, 3151, 2884, 1635, 1610, 1589, 1539, 1254, 1122, 1027, 839, 758 cm$^{-1}$; MS (FAB): m/e 391.1625 (391.1618 calc'd for $C_{18}H_{23}N_4O_6$, M+H); Anal. calc'd for $C_{18}H_{22}N_4O_6$: C, 55.38; H, 5.68; N, 14.35. Found: C, 55.24; H, 5.27; N, 14.34.

EXAMPLE 12

4,4'-Methylenebis(1-hydroxy-1-(1-ethylpropyl)-3-phenylurea)

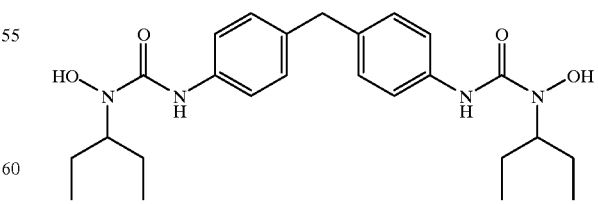

A solution of 4,4'-methylenebis(phenylisocyanate) (1.5 g, 6.0 mmol) and tetrahydrofuran (75 ml) was charged with N-(1-ethylpropyl)hydroxylamine (1.5 g, 14.5 mmol) and maintained at ambient temperature for 16 hr. The solvent was removed in vacuo to provide the crude product as a white solid. Recrystallization from ethyl acetate\hexanes provided 1.0 g of the desired product as a white powder: MP: 196.0–198.0° C. (decomp); $^1$H NMR (300 MHz, DMSO): δ 9.16 (s, 2H), 8.78 (s, 2H), 7.50 (d, J=8.5 Hz, 4H), 7.05 (d, J=8.5 Hz, 4H), 3.96–3.87 (m 2H), 3.77 (s, 2H), 1.59–1.31 (m, 8H), 0.85–0.80 (t, J=7.3 Hz, 12H); $^{13}$C NMR (75 MHz, DMSO): δ 157.7, 137.4, 134.9, 128.2, 119.1, 59.6, 24.5, 11.0; IR (KBr): 3395, 3147, 2966, 2931, 2875, 1641, 1590, 1528, 1461, 1413, 1328, 1312, 1225, 1150, 815, 761 cm$^{-1}$; MS (FAB): m/e 457.2804 (457.2815 calc'd for $C_{25}H_{37}N_4O_4$, M+H); Anal. calc'd for $C_{25}H_{36}N_4O_4$: C, 65.76; H, 7.95; N, 12.27. Found: C, 65.53; H, 7.87; N, 12.11.

EXAMPLE 13

1,1'-(m-Phenylene)bis(1-methyl-1-(3-hydroxy-3-(1-ethylpropyl)ureido)ethane)

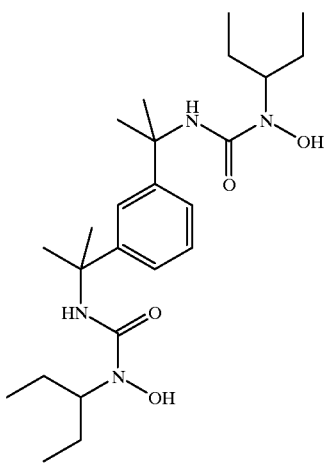

A solution of 1,3-Bis(1-isocyanato-1-methylethyl) benzene (2.3 ml, 10 mmol) and dichloromethane (100 ml) was charged with N-(1-ethylpropyl)hydroxylamine (2.2 g, 21.3 mmol). A precipitate formed immediately and the resulting mixture was maintained overnight. The precipitate was recovered by filtration and dried in vacuo to yield 4.0 g of the desired product as a white powder. Recrystallization from N,N-dimethylformamide\water provided an analytically pure sample: MP: 170.5–172.0° C.; $^1$H NMR (300 MHz, DMSO): δ 8.91 (s, 2H), 7.37 (s, 1H), 7.18 (apparent d, J=1.0 Hz, 3H), 6.53 (s, 2H), 3.75–3.65 (m, 2H), 1.57 (s, 12H), 1.51–1.30 (m, 8H), 0.80 (t, J=7.3 Hz, 12 H); $^{13}$C NMR (75 MHz, DMSO): δ 159.3, 147.7, 127.1, 122.2, 121.0, 59.5, 54.3, 29.8, 24.4, 11.2; IR (KBr): 3436, 3160, 2963, 2928, 2873, 1632, 1520, 1380, 1361, 1270, 1232, 1160, 790, 702 cm$^{-1}$; Anal. calc'd for $C_{24}H_{42}N_4O_4$: C, 63.97; H, 9.39; N, 12.43. Found: C, 63.81; H, 9.35; N, 12.48.

EXAMPLE 14

4,4'-Oxybis(1-hydroxy-1-(1-ethylpropyl)-3-phenylurea)

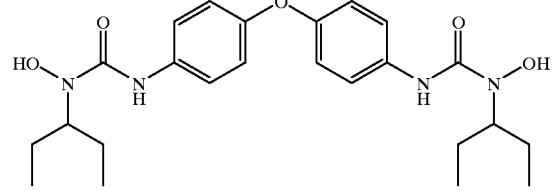

The same general procedure as reported in Example 13 was followed. 4,4'-Oxybis(phenylisocyanate) (2.52 g, 10 mmol), N-(1-ethylpropyl)hydroxylamine (2.2 g, 21 mmol), and dichloromethane (100 ml) were combined. The product formed as a precipitate. Purification by recrystallization from N,N-dimethylformamide\water yielded 3.5 g of the desired product as a white powder: MP: 182.0° C. (decomp); $^1$H NMR (300 MHz, DMSO): δ 9.16 (s, 2H), 8.89 (s, 2H), 7.58 (d, J=9.0 Hz, 4H), 6.86 (d, J=9.0 Hz, 4H), 3.98–3.88 (septet, J=4.7 Hz, 2H), 1.60–1.33 (m, 8H), 0.84 (t, J=7.3 Hz, 12 H); $^{13}$C NMR (75 MHz, DMSO): δ 157.7, 151.6, 134.9, 120.6, 118.0, 59.6, 24.5, 11.0; IR (KBr): 3405, 3138, 2967, 2929, 2875, 1638, 1591, 1533, 1503, 1461, 1412, 1243, 1221, 1161, 1106, 831, 813, 735 cm$^{-1}$; MS (FAB): m/e 459.2619 (459.2607 calc'd for $C_{24}H_{35}N_4O_5$, M+H); Anal. calc'd for $C_{24}H_{34}N_4O_5$: C, 62.86; H, 7.47; N, 12.22. Found: C, 62.56; H, 7.53; N, 12.18.

EXAMPLE 15

1,1'-(p-Phenylene)bis(3-hydroxy-3-(1-ethylpropyl) urea)

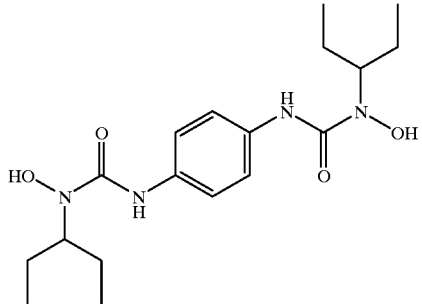

The same general procedure as reported in Example 13 was followed. 1,4-Phenylene diisocyanate (3.2 g, 20 mmol), N-(1-ethylpropyl)hydroxylamine (4.3 g, 42 mmol), and dichloromethane (200 ml) were combined. The product formed as a precipitate. Purification by recrystallization from N,N-dimethylformamide\water yielded 4.6 g of the desired product as a white powder: MP: 202.0° C. (decomp); $^1$H NMR (300 MHz, DMSO): δ 9.13 (s, 2H), 8.72 (s, 2H), 7.44 (s, 4H), 3.96–3.87 (septet, J=4.7 Hz, 2H), 1.60–1.33 (m, 8H), 0.84 (t, J=7.3 Hz, 12 H); $^{13}$C NMR (75 MHz, DMSO): δ 157.9, 134.0, 119.3, 59.6, 24.6, 11.1; IR (KBr): 3401, 3134, 2964, 2923, 2873, 1634, 1541, 1462, 1412, 1269, 1218, 1159, 1103, 1060, 833, 755, 736 cm$^{-1}$; MS (FAB): m/e 367.2331 (367.2345 calc'd for $C_{18}H_{31}N_4O_4$, M+H); Anal. calc'd for $C_{18}H_{30}N_4O_4$: C, 59.00; H, 8.25; N, 15.29. Found: C, 58.72; H, 8.34; N, 15.28.

EXAMPLE 16

1,1'-(4-Methyl-m-phenylene)bis(3-hydroxy-3-(1-ethylpropyl)urea)

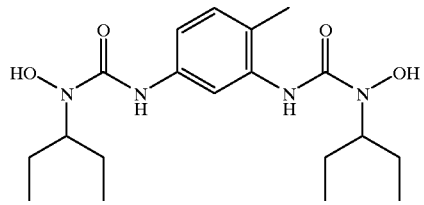

Tolylene 2,4-diisocyanate (2.9 ml, 20 mmol) was added dropwise to a solution of N-(1-ethylpropyl)hydroxylamine (4.4 g, 43 mmol) in dichloromethane (200 ml). After a few minutes, a precipitate formed. The resulting mixture was maintained overnight. Filtration followed by drying of the precipitate (in vacuo) yielded 7.5 g of the desired product as a white powder. Recrystallization from N,N-dimethylformamide\water provided an analytically pure sample: MP: 175.0–177.0° C.; $^1$H NMR (300 MHz, DMSO): δ 9.26 (s, 1H), 9.13 (s, 1H), 8.70 (s, 1H), 8.16 (s, 1H), 7.85 (d, J=2.2 Hz, 1H), 7.24 (dd, J=8.2, 2.2 Hz, 1H), 7.01 (d, J=8.5 Hz, 1H), 3.96–3.86 (m, 2H), 2.12 (s, 3H), 1.62–1.33 (m, 8H), 0.85 (t, J=7.3 Hz, 6H), 0.83 (t, J=7.3 Hz, 6H); IR (KBr): 3395, 3145, 2967, 2930, 2875, 1640, 1529, 1488, 1458, 1422, 1242, 1150, 1123, 1105 cm$^{-1}$; MS (FAB): m/e 381.2518 (381.2502 calc'd for $C_{19}H_{33}N_4O_4$, M+H); Anal. calc'd for $C_{19}H_{32}N_4O_4$: C, 59.98; H, 8.48; N, 14.72. Found: C, 59.41; H, 8.40; N, 14.75.

EXAMPLE 17

1,1'-(2-Methylpentamethylene)bis(3-hydroxy-3-(1-ethylpropyl)urea)

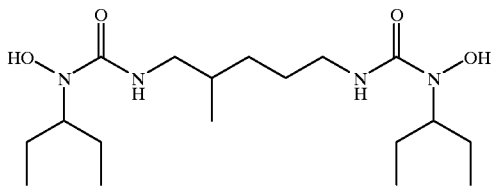

1,5-Diisocyanato-2-methylpentane (3.2 ml, 20 mmol) was added dropwise to a solution of N-(1-ethylpropyl)hydroxylamine (4.4 g, 43 mmol) in dichloromethane (200 ml). The reaction was maintained overnight and then concentrated (in vacuo) to a volume of approximately 20 ml. Purification of the sample by flash column chromatography (96:4 dichloromethane\methanol, $R_f$ 0.26) followed by recrystallization from N,N-dimethylformamide\water provided 2.6 g of the desired product as a white powder: MP: 124.0–125.0° C.; $^1$H NMR (300 MHz, DMSO): δ 8.70 (s, 1H), 8.66 (s, 1H), 6.73 (t, J=6.0 Hz, 1H), 6.68 (t, J=7.0 Hz, 1H), 3.81–3.72 (m, 2H), 3.02–2.78 (m, 4H), 1.60–0.98 (m, 13H), 0.83–0.77 (m, 15H); $^{13}$C NMR (75 MHz, DMSO): δ 160.95, 160.92, 59.9, 45.4, 39.6, 33.1, 31.2, 27.5, 24.5, 17.5, 11.1; IR (KBr): 3428, 3177, 2969, 2930, 2876, 1639, 1540, 1462, 1378, 1266, 1167, 1142, 1062, 1034, 929, 770 cm$^{-1}$; MS (FAB): m/e 375.2957 (375.2971 calc'd for $C_{18}H_{39}N_4O_4$, M+H); Anal. calc'd for $C_{18}H_{38}N_4O_4$: C, 57.73; H, 10.23; N, 14.96. Found: C, 57.90; H, 10.19; N, 14.93.

EXAMPLE 18

1,1'-Octamethylenebis(3-hydroxy-3-(1-ethylpropyl)urea)

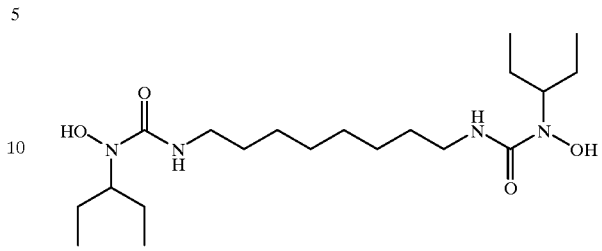

The same general procedure as reported in Example 16 was followed. 1,8-Diisocyanatooctane (3.9 ml, 20 mmol), N-(1-ethylpropyl)hydroxylamine (4.3 g, 42 mmol), and dichloromethane (200 ml) were combined to provide 7.4 g of the desired product as a white powder: MP: 89.0–90.0° C. ; $^1$H NMR (500 MHz, DMSO): δ 8.65 (s, 2H), 6.71 (t, J=5.9 Hz, 2H), 3.78 (m, 2H), 3.01 (q, J=6.7 Hz, 4H), 1.49–1.21 (m, 20H), 0.79 (t, J=7.5 Hz, 12H); $^{13}$C NMR (125 MHz, DMSO): δ 161.2, 60.1, 39.3, 29.9, 28.9, 26.3, 24.5, 11.1; IR (KBr): 3444, 3128, 2962, 2933, 2856, 1628, 1537, 1473, 1358, 1319, 1271, 1165, 1140, 1105, 1070, 1039, 927, 839, 779, 748 cm$^{-1}$; MS (FAB): m/e 403.3277 (403.3284 calc'd for $C_{20}H_{43}N_4O_4$, M+H), 300; Anal. calc'd for $C_{20}H_{42}N_4O_4$: C, 59.67; H, 10.51; N, 13.92. Found: C, 59.71; H, 10.65; N, 13.92.

EXAMPLE 19

4,4'-Methylenebis(1-hydroxy-1-(1-ethylpropyl)-3-(2-chlorophenyl)urea)

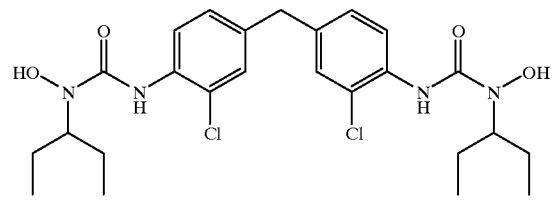

The same general procedure as reported in Example 16 was followed. 5-Methylenebis(o-chlorophenyl isocyanate) (3.19 g, 10 mmol), N-(1-ethylpropyl)hydroxylamine (2.15 g, 21 mmol), and dichloromethane (100 ml) were combined to provide 4.6 g of the desired product as a white powder: MP: 172.0–173.0° C.; $^1$H NMR (500 MHz, DMSO): δ 9.62 (s, 2H), 8.50 (s, 2H), 8.04 (d, J=8.5 Hz, 2H), 7.36 (d, J=1.8 Hz, 2H), 7.18 (dd, J=8.5, 1.8 Hz, 2H), 3.94 (septet, J=4.8 Hz, 2H), 3.85 (s, 2H), 1.56–1.39 (m, 8H), 0.83 (t, J=7.4 Hz, 12H); $^{13}$C NMR (125 MHz, DMSO): δ 157.0, 136.7, 133.6, 128.9, 128.0, 122.3, 120.8, 59.9, 38.8, 24.6, 11.0; IR (KBr): 3375, 3143, 2962, 2931, 2875, 1645, 1602, 1575, 1525, 1403, 1305, 1269, 1232, 1157, 1101, 1045, 821, 765, 736 cm$^{-1}$; MS (FAB): m/e 525.2041 (525.2035 calc'd for $C_{25}H_{35}N_4O_4Cl_2$, M+H).

5-LIPOXYGENASE INHIBITION IN HUMAN LEUKOCYTES

The test method described below measures the ability of compounds of the invention to inhibit 5-lipoxygenase activity in human leukocytes.

Blood Cell Preparation

Whole human blood is collected by venipuncture into EDTA (1.4 mL of 0.25M per 60 mL of whole blood). The red blood cells are sedimented with a 6% dextran/0.9% sodium chloride solution at a ratio of 25 mL whole blood to 15 mL dextran solution. The blood/dextran combination is mixed by inversion and the red blood cells are allowed to settle out for 45 minutes at ambient temperature. The plasma/dextran supernatant is removed then centrifuged at ambient temperature at 3000 rpm for 10 minutes. The plasma/dextran supernatant is removed and the cells are resuspended in 10 mL of the plasma/dextran solution. The cell suspension is combined with 20 mL of water, mixed for 1.5 minutes then immediately combined with 10 mL of 3.6% sodium chloride, mixed and centrifuged at ambient temperature at 3000 rpm for 10 minutes. The pellet is washed with 40 mL of Tris buffer (5.55 mM dextrose, 15.36 mM Tris base, 136.9 mM sodium chloride with pH 7.3–7.4) then centrifuged at 3000 rpm for 10 minutes. The pellet is then resuspended into Tris buffer containing 1 mM calcium chloride to provide approximately $1.0\times10^7$ cells/mL.

Compound Preparation

Compounds are dissolved in dimethyl sulfoxide. Compounds are tested at concentrations of 100, 33, 11, 3.7, 1.2 and 0.41 $\mu$M. Each concentration is tested in duplicate.

Incubation

A 15 $\mu$L portion of Tris buffer containing 1 mM calcium chloride is added to each well of a 96 well microtiter plate. A 1 $\mu$L portion of drug solution or vehicle (dimethyl sulfoxide) is added to each well followed by the addition of a 75 $\mu$L portion of the cell suspension. The plates are gently mixed then allowed to stand at ambient temperature for 10 minutes. A 10 $\mu$L portion of 30 $\mu$M A23187 Calcium Ionophore (prepared by dissolving the ionophore in DMSO and then diluting 1:80 into the Tris buffer) is added to each well except the wells that contain the blanks. The blank wells measure the level of $LTC_4$ production in the absence of A23187. The plates are gently mixed then incubated at 37° C. for 10 minutes.

Separation

Following incubation the plates are centrifuged at 2000 rpm for 1.5 minutes and the supernatant is removed as quickly as possible to stop the reaction. The supernatants are frozen at −20° C. until they are assayed.

Analysis/Calculations

The supernatants are assayed for the presence of Leukotriene $C_4$ by radioimmunoassay which is performed according to the manufacturer's instructions (Advanced Magnetics; Cambridge, Mass.). Inhibition of leukotriene biosynthesis is calculated as the ratio of the amount of $LTC_4$ formed in the presence ($LTC_4$+cpd) and absence ($LTC_4$ no cpd) of compound according to the following equation.

$$\% \text{ Inhibition} = \frac{(LTC_4 \text{ no cpd}) - (LTC_4 + \text{cpd})}{(LTC_4 \text{ no cpd})} \times 100$$

$IC_{50}$ values (concentrations of compound producing 50% leukotriene biosynthesis inhibition) are calculated by linear regression analysis of percentage inhibition versus log compound concentration plots.

A number of compounds of the invention were tested according to the above method and the results are shown in Table 1 below.

TABLE 1

5-Lipoxygenase Inhibition in Human Leukocytes

| Compound of Example | $IC_{50}$ ($\mu$M) |
|---|---|
| 4 | 4.22 |
| 5 | 0.024 |
| 6 | 0.216 |
| 7 | 5.9 |
| 8 | 5.6 |
| 9 | >10.0 |
| 10 | 0.1 |
| 11 | 0.1 |
| 12 | 0.020 |
| 13 | 65.0 |
| 14 | 0.1 |
| 15 | 2.1 |
| 16 | 58.6 |
| 17 | 12.0 |
| 18 | 0.33 |
| 19 | 0.11 |

IN VITRO HUMAN WHOLE BLOOD LEUKOTRIENE $B_4$ INHIBITION

The test method described below measures the ability of compounds to inhibit the production of Leukotriene $B_4$ in whole human blood.

Blood Cell Preparation

Whole human blood is collected by venipuncture into a 60 cc syringe containing 100 units of heparin.

Compound Preparation compounds are disolved in dimethyl sulfoxide. Compounds are tested at concentrations of 100, 33, 11, 3.7, 1.2 and 0.41 $\mu$M. Each concentration is tested in duplicate.

Incubation

Aliquots (1 $\mu$L) of compound solution are added to 1 mL polyethylene tubes followed by the addition of 500 $\mu$L portion of heparinized blood. The tubes are mixed thoroughly then allowed to preincubate at ambient temperature for 15 minutes. A 25 $\mu$L portion of 1 mM Calcium Ionophore A23187 in dimethyl sulfoxide/Tris buffer is added to the tubes. The tubes are mixed thoroughly then incubated at 37° C. for 30 minutes.

Separation

The tubes are centrifuged at 2000 rpm for 10 minutes. 100 $\mu$L portions of plasma are transferred to 1 mL polyethylene tubes containing 400 $\mu$L portions of methanol. The tubes are vortexed then frozen at −20° C. overnight.

Analysis/Calculations

The tubes are centrifuged for 10 minutes then 100 $\mu$L portions of methanol supernatant are transferred to a 96 well microtiter plate. 10 $\mu$L portions are transferred from this plate to a 96 well assay plate. Methanol dilutions of $LTB_4$ standard curve are added to the assay plate. 10 $\mu$L portions of blank methanol/plasma supernatant are added to each standard curve well. The assay plate is vacuum dried at ambient temperature. The radioimmunoassay buffer is added, the plate is bath-sonicated for 5 minutes then assayed according to the manufacturer's instructions (Advanced Magnetics; Cambridge, Mass.). Inhibition of $LTB_4$ production is calculated as the ratio of the amount of $LTB_4$ formed in the presence ($LTB_4$+cpd) and absence ($LTB_4$ no cpd) of compound according the equation below.

$$\% \text{ Inhibition} = \frac{(LTC_4 \text{ no cpd}) - (LTC_4 + \text{cpd})}{(LTC_4 \text{ no cpd})} \times 100$$

$IC_{50}$ values (concentration of compound producing a 50% inhibition of $LTB_4$ production) are calculated by linear regression analysis of percentage inhibition versus log compound concentration plots.

A number of compounds of the invention were tested according to the above method. The results are shown in Table 2 below.

TABLE 2

In Vitro Human Whole Blood Leukotriene $B_4$ Inhibition

| Compound of Example | $IC_{50}$ ($\mu$M) |
|---|---|
| 1 | 0.55 |
| 2 | 1.7 |
| 3 | 0.32 |
| 4 | 8.2 |
| 5 | 0.7 |
| 6 | 0.5 |
| 7 | 0.55 |
| 8 | 0.7 |
| 9 | 17.2 |
| 10 | 2.0 |
| 11 | 0.35 |

IN VITRO MOUSE PERITONEAL MACROPHAGE LEUKOTRIENE $C_4$ INHIBITION

The test described below measures the ability of compounds to inhibit the production of Leukotriene $C_4$ in mouse peritoneal macrophages.

Cell Preparation

Mice (female, CD-1, weighing 25 g) are euthanized by exposure to carbon dioxide. The pertoneal cavity is exposed by peeling back the abdominal skin. A 5 mL portion of media (M199 containing 1% fetal bovine serum, 100 units/mL of penicillin, 100 $\mu$g/mL streptomycin, 20 units/mL of heparin and no glutamine) is injected into the exposed peritoneal cavity of each mouse. The lavage fluid is removed and pooled to yield proximately $1 \times 10^6$ macrophages/mL. A 2 mL portion of lavage fluid is added to each well of a 24 well sterile multidish and the marcophages are allowed to adhere to the plate for 2 hours at 37° C. in a 5% carbon dioxide atmosphere. The media is removed and each well is washed with 2 mL of phosphate buffered saline (PBS). A 1 mL portion of media, without heparin, but containing 5 $\mu$Ci/mL of 3H-myoinositol is added to each well and the plates are incubated overnight at 37° C. in a 5% carbon dioxide atmosphere. The media is removed and the cells are washed twice with 2 mL portions of PBS. A 1 mL portion of Puck's saline formulation A containing 1 mM calcium chloride, 1 mM magnesium chloride and 10 mM lithium chloride is added to each well. (The Puck's formulation is made first as a 10× solution which contains 4 g of potassium chloride, 80 g of sodium chloride and 10 g of glucose per liter. The Puck's saline formulation A is made using 10 mL of the 10× Puck's formulation, 0.47 mL of 7.5% sodium bicarbonate and 2 mL of 1M N-2-hydroxyethylpiperazine-N'-2-ethanesulfonic acid per 100 mL.)

Compound Preparation

Compounds are dissolved in dimethyl sulfoxide. Compounds are tested at concentrations of 10, 1 and 0.1 $\mu$M. Each concentration is tested in duplicate.

Incubation

A 1 $\mu$L portion of compound solution or vehicle (DMSO) is added to each well and the plates are incubated for 15 minutes at 37° C. in a 5% carbon dioxide atmosphere. Zymosan is then added to provide a final concentration of 50 $\mu$g/mL in each well and the plate is incubated for 1 to 2 hours at 37° C. in a 5% carbon dioxide atmosphere.

Separation

Following incubation 200 $\mu$L portions of media are transferred to 12×75 mm tubes. The tubes are either assayed immediately or stored at −20° C. until they can be assayed.

Analysis/Calculations

The media is assayed for the presence of Leukotriene $C_4$ by radioimmunoassay which is performed according to the manufacturer's instructions (Advanced Magnetics; Cambridge, Mass.). Inhibition of $LTC_4$ production is calculated as the ratio of the amount of $LTC_4$ formed in the presence ($LTC_4$+cpd) and absence ($LTC_4$ no cpd) of compound according to the equation below.

$$\% \text{ Inhibition} = \frac{(LTC_4 \text{ no cpd}) - (LTC_4 + \text{cpd})}{(LTC_4 \text{ no cpd})} \times 100$$

$IC_{50}$ values (concentration of compound producing a 50% inhibition of $LTC_4$ production) are calculated by linear regression analysis of percentage inhibition versus log compound concentration plots.

A number of compounds of the invention were tested according to the above method. The results are shown in Table 3 below.

TABLE 3

In Vitro Mouse Peritoneal Macrophage Leukotriene $C_4$ Inhibition

| Compound of Example | Percent Inhibition | | |
|---|---|---|---|
| | 10.0 $\mu$M | 1.0 $\mu$M | 0.1 $\mu$M |
| 1 | 100 | 95 | 61 |
| 2 | 54 | 55 | 32 |
| 3 | 74 | 56 | 25 |
| 4 | 67 | 6 | −24 |
| 5 | 100 | 100 | 91 |
| 6 | 99 | 99 | 48 |
| 7 | 98 | 7 | −19 |
| 8 | 91 | 76 | 55 |
| 9 | −6 | 1 | 1 |
| 10 | 94 | 94 | 7 |
| 11 | 99 | 100 | 42 |
| 12 | 100 | 93 | 83 |

RAT EX VIVO LEUKOTRIENE $B_4$ INHIBITION

The test method described below measures the ability of a compound when administrated orally to rats to inhibit the production of Leukotriene $B_4$ in their blood which is drawn and challenged.

Rats (CD, male, non-fasted, 250 g) are lightly anesthetized with carbon dioxide and an approximately 0.75 mL sample of whole blood is obtained via cardiac puncture. The sample is dispensed into 12×75 mm polypropylene tubes containing 8–10 $\mu$L of 10,000 units/mL heparin, mixed and then maintained on ice. The rats are allowed to recover approximately one hour then dosed orally with compound dissolved in PEG 400 at a 5 mL/Kg volume. Five (5) rats are utilized per group. Two (2) hours post dose the rats are again anesthetized with carbon dioxide and the blood sampled again via cardiac puncture.

Duplicate 200 $\mu$L portions of blood are added to 1.0 mL polypropylene tubes. A 10 $\mu$L portion of 1 mM A23 187

Calcium Ionophore in dimethyl sulfoxide/Tris buffer is added to each tube. The tubes are gently vortexed then incubated in a 37° C. water bath for 30 minutes. The tubes are then centrifuged at 4000 rpm for 10 minutes. 50 µL portions of plasma are transferred to 1.0 mL tubes containing 200 µL of methanol. The tubes are vortexed then placed in the freezer overnight.

The tubes are removed from the freezer then centrifuged at 4000 rpm for 10 minutes. 20 µL portions of the methanol/plasma supernatant and 10 µl methanol dilutions of LTB$_4$ standard are transferred to 96 well v-bottom microtiter plates. The plates are vacuum dried at 40° C. A 40 µL portion of LTB$_4$ radioimmunoassay buffer is added to each well. The plate is bath sonicated for 5 minutes then assayed according to the manufacturer's instructions (Advanced Magnetics; Cambridge, Mass.). Percent inhibition values are obtained by comparing the level of LTB$_4$ in the post-dose samples to the level in the pre-dose samples according to the equation below.

$$\% \text{ Inhibition} = \frac{(LTB_4 \text{ pre-dose}) - (LTB_4 \text{ post-dose})}{(LTB_4 \text{ pre-dose})} \times 100$$

A number of compounds of the invention were tested. The results are shown in Table 4 below.

TABLE 4

Rat Ex Vivo Leukotriene B$_4$ Inhibition

| Compound of Example | Dose (mg/Kg) | % Inhibition |
|---|---|---|
| 1 | 10 | 16 |
| 1 | 50 | 93 |
| 2 | 50 | 34 |
| 3 | 50 | 6 |
| 7 | 50 | 59 |
| 9 | 50 | 4 |
| 10 | 50 | 8 |
| 11 | 50 | 4 |
| 12 | 50 | 15 |

The foregoing specification and examples provide a complete description of the invention, which resides in the following claims.

The claimed invention is:

1. A pharmaceutical composition comprising
   (i) a pharmaceutically acceptable vehicle; and
   (ii) a therapeutically effective amount of a compound of the formula (I)

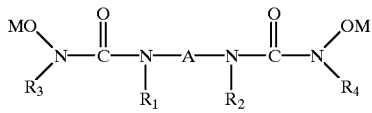

(I)

or a pharmaceutically acceptable salt thereof, wherein
   M is selected from the group consisting of hydrogen, a pharmaceutically acceptable cation, and a pharmaceutically acceptable metabolically cleavable group;
   $R_1$ and $R_2$ are independently selected from the group consisting of hydrogen and $C_{1-6}$ straight or branched chain alkyl;
   $R_3$ and $R_4$ are independently selected from the group consisting of $C_{1-14}$ straight or branched chain alkyl optionally substituted by a group selected from halogen, nitro, hydroxyl, carboxyl and amino, and optionally interrupted by —O—, —S(O)$_{0-2}$—, —NR— wherein R is as defined below, or —CO—; and arylalkyl wherein the alkyl group is straight or branched chain and has from one to eight carbon atoms and the aryl group is phenyl optionally substituted with one or more substituents selected from the group consisting of $C_{1-6}$ straight or branched chain alkyl and halogen;
   A is selected from the group consisting of:
   (a) phenylene optionally substituted with one or more substituents selected from the group consisting of $C_{1-6}$ straight or branched chain alkyl and halogen;
   (b) naphthalene optionally substituted with one or more substituents selected from the group consisting of $C_{1-6}$ straight or branched chain alkyl and halogen;

(c)

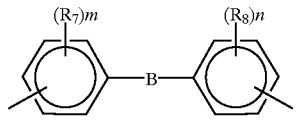

wherein
   each $R_7$ and $R_8$ is independently selected from the group consisting of hydrogen, $C_{1-3}$ straight or branched chain alkyl, $C_{1-3}$ straight or branched chain alkoxy, and halogen;
   m is 1 or 2;
   n is 1 or 2; and
   B is selected from the group consisting of
   (i) a carbon-carbon bond,
   (ii) oxy,
   (iii) thio,
   (iv) sulfone,
   (v) carbonyl, (vi)

wherein
   R is selected from the group consisting of hydrogen and $C_{1-3}$ straight or branched chain alkyl,
   (vii) —(CH$_2$)$_p$— wherein p is an integer from 1 to 14, and (viii)

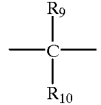

wherein $R_9$ and $R_{10}$ are independently selected from the group consisting of hydrogen, $C_{1-3}$ straight or branched chain alkyl, $C_{3-6}$ cycloalkyl; and trifluoromethyl.

2. A method of inhibiting the enzyme 5-lipoxygenase in an animal comprising administering to the animal, in an amount effective to inhibit the enzyme 5-lipoxygenase, a compound of the formula (I)

(I)

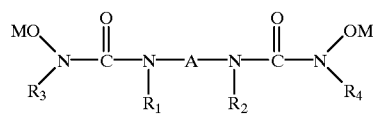

or a pharmaceutically acceptable salt thereof, wherein
M is selected from the group consisting of hydrogen, a pharmaceutically acceptable cation, and a pharmaceutically acceptable metabolically cleavable group;
$R_1$ and $R_2$ are independently selected from the group consisting of: hydrogen and $C_{1-6}$ straight or branched chain alkyl;
$R_3$ and $R_4$ are independently selected from the group consisting of $C_{1-14}$ straight or branched chain alkyl optionally substituted by a group selected from halogen, nitro, hydroxyl, carboxyl and amino, and optionally interrupted by —O—, —S(O)$_{0-2}$—, —NR— wherein R is as defined below, or —CO—; and arylalkyl wherein the alkyl group is straight or branched chain and has from one to eight carbon atoms and the aryl group is phenyl optionally substituted with one or more substituents selected from the group consisting of $C_{1-6}$ straight or branched chain alkyl and halogen;
A is selected from the group consisting of:
(a) phenylene optionally substituted with one or more substituents selected from the group consisting of $C_{1-6}$ straight or branched chain alkyl and halogen;
(b) naphthalene optionally substituted with one or more substituents selected from the group consisting of $C_{1-6}$ straight or branched chain alkyl and halogen;

(c)

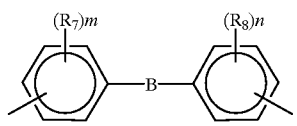

wherein
each $R_7$ and $R_8$ is independently selected from the group consisting of hydrogen, $C_{1-3}$ straight or branched chain alkyl, $C_{1-3}$ straight or branched chain alkoxy, and halogen;
m is 1 or 2;
n is 1 or 2; and
B is selected from the group consisting of
(i) a carbon-carbon bond,
(ii) oxy,
(iii) thio,
(iv) sulfone,
(v) carbonyl, (vi)

wherein
R is selected from the group consisting of hydrogen and $C_{1-3}$ straight or branched chain alkyl,
(vii) —(CH$_2$)$_p$— wherein p is an integer from 1 to 14, and (viii)

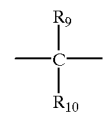

wherein $R_9$ and $R_{10}$ are independently selected from the group consisting of hydrogen, $C_{1-3}$ straight or branched chain alkyl, $C_{3-6}$ cycloalkyl, and trifluoromethyl.

3. A method of treating in an animal a condition responsive to the inhibition of the enzyme 5-lipoxygenase comprising administering to the animal, in an amount effective to inhibit the enzyme 5-lipoxygenase, a compound of the formula (I)

(I)

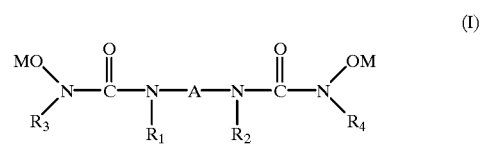

or a pharmaceutically acceptable salt thereof, wherein
M is selected from the group consisting of hydrogen, a pharmaceutically acceptable cation, and a pharmaceutically acceptable metabolically cleavable group;
$R_1$ and $R_2$ are independently selected from the group consisting of hydrogen and $C_{1-6}$ straight or branched chain alkyl;
$R_3$ and $R_4$ are independently selected from the group consisting of $C_{1-14}$ straight or branched chain alkyl optionally substituted by a group selected from halogen, nitro, hydroxyl, carboxyl and amino, and optionally interrupted by —O—, —S(O)$_{0-2}$—, —NR— wherein R is as defined below, or —CO—; and arylalkyl wherein the alkyl group is straight or branched chain and has from one to eight carbon atoms and the aryl group is phenyl optionally substituted with one or more substituents selected from the group consisting of $C_{1-6}$ straight or branched chain alkyl and halogen;
A is selected from the group consisting of:
(a) phenylene optionally substituted with one or more substituents selected from the group consisting of $C_{1-6}$ straight or branched chain alkyl and halogen;
(b) naphthalene optionally substituted with one or more substituents selected from the group consisting of $C_{1-6}$ straight or branched chain alkyl and halogen;

(c)

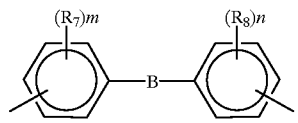

wherein
each $R_7$ and $R_8$ is independently selected from the group consisting of hydrogen, $C_{1-3}$ straight or branched chain alkyl, $C_{1-3}$ straight or branched chain alkoxy, and halogen;
m is 1 or 2;
n is 1 or 2; and
B is selected from the group consisting of (i) a carbon-carbon bond,
(ii) oxy,
(iii) thio,
(iv) sulfone,
(v) carbonyl, (vi)

wherein
R is selected from the group consisting of hydrogen and C$_{1-3}$ straight or branched chain alkyl,
(vii) —(CH$_2$)$_p$— wherein p is an integer from 1 to 14, and (viii)

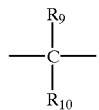

wherein R$_9$ and R$_{10}$ are independently selected from the group consisting of hydrogen, C$_{1-3}$ straight or branched chain alkyl, C$_{3-6}$ cycloalkyl, and trifluoromethyl.

4. A method according to claim 3, wherein the condition responsive to the inhibition of the enzyme 5-lipoxygenase is selected from the group consisting of adult respiratory distress syndrome, allergic rhinitis, arthritis, asthma, cancer, chronic obstructive pulmonary disease, gout, inflammatory bowel disease, ischemic induced myocardial injury, psoriasis, reperfusion injury, spinal cord injury, stroke, and traumatic brain injury.

5. A method according to claim 3, wherein the condition responsive to the inhibition of the enzyme 5-lipoxygenase is an inflammatory disease.

6. A method according to claim 3, wherein the condition responsive to the inhibition of the enzyme 5-lipoxygenase is asthma.

* * * * *